United States Patent [19]

Litman et al.

[11] Patent Number: 5,030,558
[45] Date of Patent: Jul. 9, 1991

[54] QUALITATIVE IMMUNOCHROMATOGRAPHIC METHOD AND DEVICE

[75] Inventors: David J. Litman, Los Altos; Thomas M. Li, Milpitas; Laura L. Buelteman, San Jose; Emmy T. Wong, Los Alto Hills, all of Calif.

[73] Assignee: Syntex (U.S.A.) Inc., Palo Alto, Calif.

[21] Appl. No.: 928,233

[22] Filed: Nov. 7, 1986

[51] Int. Cl.$^5$ ............... G01N 33/543; G01N 33/558
[52] U.S. Cl. ..................... 435/7.91; 422/56; 422/58; 435/805; 435/970; 435/7.92; 436/501; 436/514; 436/518; 436/530; 436/805; 436/810; 436/815; 436/816; 436/822
[58] Field of Search ............... 422/56, 58; 435/7, 805, 435/810; 436/501, 518, 530, 810, 815, 822, 514, 805, 816

[56] References Cited

U.S. PATENT DOCUMENTS

| | | | |
|---|---|---|---|
| 3,720,760 | 3/1973 | Bennich et al. | 436/513 |
| 3,990,850 | 11/1976 | Friedman et al. | 436/183 |
| 3,992,631 | 11/1976 | Harte | 436/815 |
| 4,055,394 | 10/1977 | Friedman et al. | 422/56 |
| 4,094,647 | 6/1978 | Deutsch et al. | 422/56 |
| 4,160,008 | 7/1979 | Fenocketti et al. | 422/56 |
| 4,163,779 | 8/1979 | Harte et al. | 436/527 |
| 4,168,146 | 9/1979 | Grubb et al. | 422/56 |
| 4,189,304 | 2/1980 | Adams, Jr. et al. | 422/56 |
| 4,207,307 | 6/1980 | Kaul et al. | 436/819 |
| 4,327,073 | 4/1982 | Huang | 422/66 |
| 4,361,537 | 11/1982 | Deutsch et al. | 422/56 |
| 4,366,241 | 12/1982 | Tom et al. | 435/7 |
| 4,384,958 | 5/1983 | Wisebaker et al. | 422/70 |
| 4,434,236 | 2/1984 | Freytag et al. | 436/512 |
| 4,435,504 | 3/1984 | Zuk et al. | 436/530 |
| 4,438,067 | 3/1984 | Siddiqi | 422/56 |
| 4,540,659 | 9/1985 | Litman et al. | 436/824 |
| 4,740,468 | 4/1988 | Weng et al. | 436/514 |

FOREIGN PATENT DOCUMENTS

| | | |
|---|---|---|
| 0100619 | 2/1984 | European Pat. Off. . |
| 0160467 | 11/1985 | European Pat. Off. . |
| 0183442 | 6/1986 | European Pat. Off. . |
| 0191640 | 8/1986 | European Pat. Off. . |
| 48-5925 | 1/1973 | Japan . |
| 84/02193 | 6/1984 | PCT Int'l Appl. . |
| 8702774 | 5/1987 | World Int. Prop. O. . |

Primary Examiner—Esther M. Kepplinger
Assistant Examiner—David A. Launders
Attorney, Agent, or Firm—Theodore J. Leitereg; Gerald F. Swiss

[57] ABSTRACT

A method for determining the presence of a predetermined minimum detectible amount of one or more analytes in a sample suspected of containing the analyte is disclosed. Each analyte is a member of a specific binding pair ("sbp member") consisting of ligand and its complementary receptor. The method comprises contacting with a test solution containing the sample and predetermined amounts of two or more of a plurality of first sbp members, each respectively analogous to one of the analytes, a contact portion of a piece of bibulous material capable of being traversed in at least one direction by the test solution by capillary migration. The bibulous material contains predetermined amounts of two or more of a plurality of second sbp members, each respectively capable of binding one of the analytes and corresponding first sbp member. The second sbp members are non-diffusively bound to the bibulous material at least between the contact portion and a predetermined site on the piece of bibulous material separated from the contact portion such that in the presence of a predetermined amount of one or more analytes the analogous first sbp member migrates at least to the predetermined site on the piece of bibulous material. Next, at least a portion of the test solution is allowed to transverse the bibulous material by means of capillary migration. The predetermined site is examined for the presence of one or more of the first sbp members.

36 Claims, No Drawings

QUALITATIVE IMMUNOCHROMATOGRAPHIC METHOD AND DEVICE

BACKGROUND OF THE INVENTION

1. Field of the Invention

The ability to employ naturally occurring receptors or antibodies directed to specific compounds in assaying for the presence of a compound of interest has created a burgeoning immunoassay business. In each of the assays, a homologous pair of specific binding pair ("sbp") members, usually an immunological pair, involving a ligand and a receptor (antiligand) is involved, wherein one of the sbp members is labeled with a label which provides a detectible signal. The immunoassay methodology results in a distribution of the signal label between signal label bound in a complex of the sbp members and unbound signal label. The differentiation between bound and unbound signal label can be as a result of physical separation of bound from unbound signal label or modulation of the detectible signal between bound and unbound signal label.

For the most part, immunoassays have been directed to quantitative determination of a wide variety of compounds of interest in clinical laboratories requiring relatively sophisticated equipment and careful technique. Immunoassays have found less extensive commercial application where semi-quantitative or qualitative results would be acceptable and the determination would involve non-laboratory personnel, such as in a home or a medical practitioner's office. Even in the clinical laboratory, simple and rapid screening tests employing inexperienced personnel could serve to provide substantial economies.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Other factors include the ease of preparation of the reagents, the precision with which samples and reagent solutions must be prepared and measured, the storage stability of the reagents, the number of steps required in the protocol, and the proficiency and accuracy with which each of the steps must be performed. Therefore, in developing an assay that can have application with untrained personnel, such as assays to be performed in the home, in forensic medicine, by medical practitioners, or the like, the observed result should be minimally affected by variations in the manner in which the protocol is carried out and the techniques for performing the various steps should be simple.

In general, immunoassays that permit the simultaneous determination of two or more analytes have been difficult to design and those that have been demonstrated utilize different radioactive labels on separate analyte analogs.

2. Description of the Prior Art

A test device for determining a characteristic of a sample, particularly for determining substances in fluid samples, is disclosed in U.S. Pat. No. 4,094,647. A thin layer chromatography device and method of making a chromatography test is disclosed in U.S. Pat. No. 4,384,958. An immunoassay wherein labeled antibody is displaced from immobilized analyte analog is described in U.S. Pat. No. 4,434,236. A device and method for detecting myoglobin is disclosed in U.S. Pat. No. 4,189,304. Test strips for analyzing substances dissolved in liquids are described in U.S. Pat. No. 4,438,067. A multi-layered test device for determining the presence of a liquid sample component and the method of using such a device, are described in U.S. Pat. No. 4,160,008. A method for measuring antigen by labeled antigen using insoluble antibody is disclosed in Japanese Patent Application Laid-Open No. 5925/73-Jan. 25, 1973.

A concentrating zone method in heterogeneous immunoassays is disclosed in U.S. Pat. No. 4,366,241. U.S. Pat. No. 4,168,146 describes an immunoassay test strip. U.S. Pat. Nos. 3,990,850 and 4,055,394 describe diagnostic test cards. An automated method for quantitative analysis of biological fluids is described in U.S. Pat. No. 4,327,073. A chromogenic support immunoassay is disclosed in International Application No. PCT/US83/01887.

A wide variety of patents and patent applications provide an extensive literature of different techniques for producing detectible signals in immunoassays. The following list is merely illustrative of some of these techniques which can find application in this invention. The following is a list of U.S. patents and patent applications and a general statement of the type of label involved: U.S. Pat. Nos. 3,646,346, Radioactive Label; 3,654,090, 3,791,932 and 3,817,838, Enzyme Labels; 3,996,345, Fluorescer-Quencher Labels; 4,062,733, Radioactive Label; 4,067,959, Fluorescer or Enzyme Label; 4,104,029, Chemiluminescent Label; and 4,160,645, Non-Enzymatic Catalyst Label. See U.S. Pat. Nos. 3,966,879 for an electrophoretic technique employing an antibody zone and U.S. Pat. No. 4,120,945 for an RIA where labeled analyte is initially bound to a solid support through antibody. U.S. Pat. No. 4,233,402 employs enzyme pair labels; U.S. Pat. No. 4,720,450, chemically induced fluorescent labels; and U.S. Pat. No. 4,287,300, enzyme anionic charge labels.

SUMMARY OF THE INVENTION

The methods and devices of the present invention are useful for determining the presence of predetermined minimum detectible amounts of one or more of a plurality of analytes in a sample suspected of containing one or more of the analytes. The device is a piece of bibulous material capable of being traversed in at least one direction by a test solution through capillary migration. The test solution is comprised of the sample and predetermined amounts of two or more first sbp members, each respectively analogous to one of the analytes. The bibulous material contains predetermined amounts of two or more of a plurality of second sbp members substantially uniformly and non-diffusively bound thereto at least between a contact portion thereof and a predetermined site on the piece of bibulous material separated from the contact portion. The second sbp members are each respectively capable of binding one of the analytes and corresponding first sbp member. In the presence of a predetermined amount of one or more of the analytes, the analogous first sbp member migrates to the predetermined site. The device can include means associated therewith for allowing detection of one or more of the first sbp members only at the predetermined site.

In the method the contact portion of the piece of bibulous material separated from the predetermined site is contacted with the above test solution, which traverses the bibulous material by means of capillary action. At least a portion of the test solution is allowed to traverse the bibulous material. The predetermined site is examined for the presence of the first sbp member, which is usually indicated by the presence of a detectible signal. Such signal can be detected directly or the predetermined site can be exposed to a signal producing means capable of interacting with the first sbp members to produce a detectible signal. The presence of a signal at the predetermined site indicates the presence of one or more analytes in the test solution.

The method and device of the present invention are advantageous because the device and method are simple to use and can be applied to a plurality of analytes in a single test solution. The presence of one or more analytes in the test solution can be readily determined using a single piece of bibulous material and appropriate first and second sbp members.

DESCRIPTION OF THE SPECIFIC EMBODIMENTS

As mentioned above, the present invention is directed to methods and devices for determining the presence of predetermined minimum detectible amounts of one or more of a plurality of analytes in a sample suspected of containing one or more of the analytes. A test solution is formed by combining in an aqueous medium the sample and a predetermined amount of at least two or more first sbp members, each analogous to one of the analytes, usually a conjugate of one of the analytes and a label. A portion, i.e., the "contact portion", usually an end portion of a piece, usually a strip, of bibulous material capable of being traversed in at least one direction by the test solution by means of capillary migration is contacted with the test solution. The bibulous material contains predetermined amounts of at least two or more second sbp members, each respectively capable of binding to one of the analytes and a corresponding first sbp member. The second sbp members are substantially uniformly and non-diffusively bound to the bibulous material at least between the contact portion and a predetermined site separated from the contact portion such that only in the presence of a predetermined amount of one or more of the analytes does a first sbp member migrate to the predetermined site. At least a portion of the test solution is allowed to traverse the bibulous material by capillary action. Next, any first sbp member bound to the predetermined site is detected. Detection may be achieved directly, for example, when the first sbp member is labeled with a radioactive label, or the predetermined site can be exposed to a signal producing means such as light, heat or a chemical reagent capable of interacting with the label to produce a signal in relation to the amount of one or more of the analytes in the test solution. Any signal produced at the predetermined site is then detected. The device can have means associated therewith for allowing detection of the first sbp members only at the predetermined site. In the presence of one or more of the analytes in the sample, one or more of the first sbp members migrates to the predetermined site. The signal producing means is reactive with the first sbp members and includes reagents required to produce a detectible signal at the predetermined site when one or more of the analytes is present in a predetermined amount in the sample.

Before proceeding further with the description of the specific embodiments of the present invention, a number of terms will be defined.

Analyte —the compound or composition to be measured that is capable of binding specifically to an antibody, usually an antigen or drug.

The precise nature of the antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes are characterized by having single binding sites (monovalent) or multiple binding sites (polyvalent). The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes, and the like.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member") —one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the definition.

Ligand —any organic compound for which a receptor naturally exists or can be prepared.

Receptor ("antiligand") —any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq. and the like.

Labeled sbp member —a label, generally capable of electrochemical detection or absorption or emission of electromagnetic radiation, a catalyst, frequently an enzyme, bound to a first sbp member. The labeled sbp member is a member of the signal producing system and the first sbp member is chosen to bind to the second sbp member in accordance with a particular protocol in an assay.

Antibody —an immunoglobulin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for the analyte —an antibody specific for an analyte.

First sbp member —a modified analyte or analyte analog or surrogate which can compete with the analogous analyte in binding to a second sbp member, usually a receptor or antibody, the modification providing means to join the analyte analog to a label to provide a labeled sbp member. The analyte analog will usually differ from the analyte by more than replacement of a hydrogen with a bond which links the analyte analog to a hub or label, but need not. The term analyte surrogate refers to a compound having the capability of binding the antibody for the analyte. Thus, the analyte surrogate may bind to the antibody for the analyte in a manner similar to the analyte. On the other hand, the surrogate could be, for example, an antibody directed against the idiotype of an antibody to the analyte.

Second sbp member —an sbp member capable of binding to the analyte and the first sbp member. The second sbp member can bind to a determinant site on the analyte and to a determinant site on the first sbp member. A preferred second sbp member is an antibody.

Bibulous material —a porous material having pores of at least $0.1\mu$, preferably at least $1.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit covalent bonding of receptors or antibodies as well as to permit bonding of other compounds which form a part of the signal producing system.

Binding of receptors and antibodies to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The piece of bibulous material can be a single structure such as a sheet cut into strips or it can be several strips or particulate material bound to a support or solid surface such as found, for example, in thin-layer chromatography and may have an absorbent pad either as an integral part or in liquid contact. The piece of bibulous material can also be a sheet having lanes thereon, capable of spotting to induce lane formation, wherein a separate assay can be conducted in each lane. The piece of bibulous material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips of bibulous material will be described by way of illustration and not limitation.

The support for the bibulous material, where a support is desired or necessary, will normally be water insoluble, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the bibulous materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like. The absorbent pad may be any hydrophilic bibulous material such as paper, sponge, felt, porous polymers and the like.

Label —A label may be any molecule bound to the first sbp member that is required to produce a signal. In the subject invention, the label may be inert and serve solely as a binding site for a member of the signal producing means or it may spontaneously produce a detectable signal or may produce a detectable signal in conjunction with a signal producing means. The label may be isotopic or nonisotopic, preferably nonisotopic. However, an isotopic label can be preferred for achieving high sensitivity when using radio-autographic detections with photographic film.

Signal producing means —means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the bibulous material.

Signal producing system —The signal producing system may have one or more components, at least one component being the labeled sbp member. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal producing system can include at least one catalyst as a label, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal at the predetermined site, related to the presence of label at the predetermined site.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the compound that produces a signal to provide the compounds that generates the signal.

Where two enzymes are employed, the involved reactions will be, for the most part, hydrolysis or redox reactions. In the case of hydrolysis, a derivatized dye precursor that has a hydrolytically labile bond, the hydrolytic enzyme and an enzyme that catalyzes the released dye precursors to a dye conversion product is illustrative of this type of system. In redox reactions, a first enzyme can produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the bibulous material, while the other enzyme is the label conjugated to the analyte.

Additionally, one or more other members of the signal producing system can be bound to the bibulous material depending on the particular signal producing system chosen or the particular protocol followed.

In order to have a detectable signal, it is desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably, hydrolases such as alkaline phosphatase and $\beta$-galactosidase. Alternatively luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly, non-ionic surfactants, binding enhancers, e.g. polyalkylene glycols, or the like.

Means associated with the bibulous material for allowing detection of one or more of the first sbp members only at the predetermined site—such means can take the form of an enclosure that conceals from view portions of the bibulous material that may have one or more of the first sbp members bound thereto other than the predetermined site. Usually, the portion of the bibulous material between the contact portion and the predetermined site is concealed from view by the enclosure. Such enclosure can surround the bibulous material and have an opening or window for viewing the predetermined site. The enclosure can be fabricated of any inert material such as plastic, glass, and the like, preferably plastic. The dimensions of the enclosure will be determined by the dimensions of the bibulous material. The size of the opening will also be determined by the dimensions of the bibulous material with a primary consideration being that a sufficient area of the predetermined site be viewed in order to accurately observe whether or not a signal is present. The opening will generally be found along the face of the bibulous material corresponding to the placement of the predetermined site. The enclosure will also have an opening at or near the contact portion of the piece of bibulous material to provide entry of the test solution and other liquid reagents.

In another embodiment such means can be a signal inhibitor that is bound to the bibulous material at sites other than the predetermined site that can come in contact with first sbp members in carrying out the assay. As a result, signal will only be formed and detected at the predetermined site. The signal inhibitor is selected based on the signal producing means employed. The signal inhibitor can interact with the signal producing means to delay signal formation for a period of time or to completely inhibit signal formation. For example, where a catalyst such as an enzyme is employed as a label, the signal inhibitor can be an alternate substrate for the catalyst or a compound that reacts with the product of the catalyst and its substrate. Ascorbic acid or a salt or ester thereof, can be employed as a signal inhibitor for a peroxidase enzyme. Other examples of signal inhibitors are ferricyanide, uric acid, hydroquinones, glutathione, dithiothreitol, sodium sulfite, and the like. The amount of signal inhibitor will be determined by the amount of the corresponding signal producing system member used in the assay. Generally, the amount of signal inhibitor is sufficient to inhibit signal production at other than the predetermined site for a period long enough to detect the signal at the predetermined site.

In the method of the invention, at least two first sbp members, each analogous to one of the analytes suspected of being present in a sample, are combined in an aqueous medium with the sample to provide an aqueous test solution. The primary consideration is that a test solution containing the sample and the first sbp members come in contact with the contact portion of the strip and traverse the strip through capillary action. This traversal can be upward, downward, horizontal or combinations thereof. Whether one of the first sbp members migrates to a predetermined site is related to the presence in the sample of the corresponding analyte in an amount exceeding the predetermined minimum detectible amount of that analyte.

After the strip has been contacted with the test solution and capillary migration is allowed to occur, the strip is exposed to the signal producing means. Depending on the label and the signal producing means, such exposure may be the result of irradiation, heating, or contact with chemical agents. In the latter instance at least the predetermined site will be contacted with a developer solution containing the chemical agents. The signal producing system provides a detectible signal if one or more of the first sbp members is present at the predetermined site.

The solvent for the test solution and/or the developer solution will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself.

The pH for the medium will usually be in the range of 4–11, more usually 5–10, and preferably in the range of about 6–9. The pH is chosen to maintain a significant site of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably, from about 0.05 to 0.5 weight percent of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 4°–50° C., more usually in the range of about 10°–40° C., and frequently will be ambient temperatures, that is, about 15°–25° C.

The concentration in the aqueous test solution of analyte that may be assayed will generally vary from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

The size of the strip is dependent on several considerations. The primary consideration is to move a sufficient amount of one or more of the first sbp members to the predetermined site when one or more of the analytes are in the test solution to give a sufficient signal so that a sensitive and accurate assay is achieved. When capillary flow is predominantly upward, the length and thickness of the strip control the amount of solution that can pass along the strip. If the transfer of a large volume of test solution is desired, the fluid capacity of the strip above the predetermined site must be sufficient to accommodate the desired volume. If the strip is used to provide a predominantly downward flow so as to syphon the test solution, this volume requirement is not needed. Moreover, if an absorbent material is provided to contact the end of the strip not used to contact the test solution, the volume requirement is also eliminated. In general, for upward flow strips the fluid retention volume will be usually greater than 20 μL, preferably at least 50–200 μL. For downward flow strips retention volumes as low as 2–20 μL can be used but volumes of 20–200 μL are preferable.

Thickness of the strips is not critical and will normally be 0.1–2 mm, usually 0.15–1 mm, preferably 0.2–0.7 mm. Generally, the minimum thickness is dictated by the strength of the material and the need to produce a readily detectable signal whereas the maximum width will be dictated by convenience of handling and cost of the reagents.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The cross-sectional dimensions of a strip have been described in the preceding discussion in terms of a rectangle for purposes of illustration and not limitation. As mentioned above, other cross-sectional shapes such as circular, triagonal, oval, etc, fall equally within the scope of this invention. The dimensions thereof can be determined by those skilled in the art with reference to the disclosure herein.

The length of the strip will depend on the concentration of one or more of the analytes and practical considerations such as ease of handling and will be about 1 cm to 40 cm, usually about 2 cm to 25 cm, preferably about 4 to 20 cm but may be of any practical length. The structure of the strip can be varied widely and includes fine, medium fine, medium, medium coarse and coarse. In general, smaller pore size and finer material will provide slow capillary flow and efficient capture of bound conjugate on the strip. Courser more porous materials provide faster flow, but the efficiency of capture is reduced. Selection of the porosity of the material depends on the rate of binding of the components for a given assay.

The position of the predetermined site is governed by the basic principle involved in the present invention. The minimum distance from the contact portion is determined by the capacity of the intervening bibulous material to non-diffusively bind the second sbp members. Thus, the minimum amount of each sbp member that must be bound is equivalent to the predetermined minimum detectible analyte amount. The first sbp member will bind to the second sbp member over some length of the strip distal to the contact portion when no analyte is present. Since this distance will increase when analyte is present it is obvious that the predetermined site must be located an additional distance away from the contact end in order to avoid false positive assay results. If very sensitive detection is required, it may be desirable to place the predetermined site only slightly more distant. When sensitivity is not critical, it may be desirable to position the predetermined site close to the end of the strip which is opposite to the contact portion of the strip. Desirably, the predetermined site should be at least 10 mm, preferably at least 30 mm, from the contact portion of the strip. It may be positioned any greater distance away from the end provided the test solution can pass thereto by capillary action and carry along unbound first sbp members. In this way, the predetermined site is "separated" from such end portion.

Other reagents, which are members of the signal producing system, can vary widely in concentration depending upon the particular protocol and their role in signal production. The amounts of the first and second sbp members are selected based on the predetermined minimum detectible amounts of the analytes that are in the test solution and the position of the predetermined site. The concentrations of each of the first sbp members in the test solution will usually not exceed the concentration of the corresponding analyte in the test solution that results from the inclusion in the test solution of the predetermined minimum detectible amount of the analyte. Preferably the concentration of the first sbp member will be 5 to 20 times lower than the corresponding concentration of analyte. In general, the amounts of the first sbp members are chosen such that in the absence of all analytes none of the first sbp members migrates to the predetermined site.

The second sbp members are substantially uniformly bound to the strip. The amount of each second sbp member bound between the contact portion and the predetermined site must be about equivalent to the predetermined minimum detectible amount of analyte plus the amount of the corresponding first sbp member in the test solution. If it is desired to move the predetermined site away from the contact portion, it is, therefore, only necessary to reduce the density of each second sbp member on the strip. Conversely, the predetermined site can be moved closer to the contact portion by increasing the density of the second sbp members on the strip.

In carrying out the assay, the protocol will normally involve combining in an aqueous medium the sample suspected of containing the analytes with the corresponding first sbp members to form the aqueous test solution. The sample may be derived from a wide variety of sources, such as physiologic fluids, illustrated by saliva, blood, serum, plasma, urine, ocular lens fluid, spinal fluid, etc., food products such as milk and wine, chemical processing streams, food waste water, etc.

The contact portion of the strip, usually an end portion, is contacted with the test solution, usually by immersion of the contact portion into the test solution. However, contact of the bibulous material with the test solution can be carried out by other techniques such as by spotting the test solution on the bibulous material. This technique has particular application to pieces of bibulous material that are circular, oval, sheet-like, etc. Wetting of the strip by capillary action usually is allowed to continue at least until the predetermined site is wet. Usually, most of the strip becomes wetted by the test solution.

For the most part, relatively short times are involved for the test solution to traverse the strip. Usually, the traverse of the test solution over the strip will take at least 30 sec and not more than 1 hour, more usually from about 1 min to 30 min. When an enzyme is used in the signal producing means, the development of the signal will generally range from 30 sec to 30 min, more usually from about 30 sec. to 5 min.

After the liquid has traversed the strip, the predetermined site is examined for the presence of a detectible signal. Where the signal is the result of a radioactive label or the like, the signal can be detected directly. Where chemical agents form part of the signal producing means that includes the label, the contact portion of the strip can be immersed into the developer solution, which is allowed to wick along the strip to the predetermined site. Alternatively, the predetermined site can be contacted directly with the developer solution such as by spotting.

When an enzyme is used as a label, the substrate will normally be in substantial excess in the developer solution, so as not to be rate limiting (greater concentration than Km). The developer solution will usually be appropriately buffered for the enzyme system.

After contacting the predetermined site with the developer solution, the strip is contacted with any remaining members of the signal producing system not present in the developer or test solutions or present on the strip. A sufficient time is allowed to elapse prior to measuring the signal to produce an amount of the signal producing compound. Once the detectable signal has been produced, it is known that at least one of the analytes in the sample is present at or above the predetermined minimum detectible amount.

The strip can be coated with a wide variety of materials to provide for enhanced properties. Coatings may include protein coatings, polysaccharide coatings, synthetic polymers, sugars or the like, which are used particularly to enhance the stability of the materials conjugated to the strip. These compounds can also be used for improved binding of the materials, such as antibody binding or the like.

The strip can be activated with reactive functionalities to provide for covalent bonding of the organic materials to be conjugated to the strip such as those described in U.S. Pat. No. 4,168,146, the relevant disclosure of which is incorporated herein by reference.

The second sbp member and, where desired, members of the signal producing system, can be bound to the strip by adsorption, rather than covalent bonding, as long as such binding is non-diffusive. This will involve contacting the bibulous support with a solution containing the materials to be bound to the strip and allowing the strip to dry. In general, this procedure will be useful only where the bibulous support is relatively hydrophobic or has a high surface charge, and subsequent treatment with proteins, detergents, polysaccharides, or other materials capable of blocking non-specific binding sites may be required.

In a preferred embodiment of this invention a sample suspected of containing one or more of a plurality of drugs can be screened for the presence of one or more of the drugs. A test solution is formed by mixing together in an appropriate liquid medium the sample and at least two or more first sbp members, e.g., conjugates each comprising one of the drugs and a label, which can be the same or different for each conjugate. The result of the assay will indicate whether any one of the drugs is present such as in a screening assay but not which one of the drugs is present.

For example, in one embodiment of the present invention there are two analytes that are monovalent drugs. The sample suspected of containing the drugs is mixed with predetermined amounts of conjugates of an enzyme with one of each of the drugs to form the aqueous test solution. The bibulous strip has homogeneously bound thereto predetermined amounts of antibodies for each of the drugs. As a consequence, the drugs in amounts below the predetermined minimum detectible amounts and the conjugates are captured prior to the test solution reaching a predetermined site when the contact portion is contacted with the test solution. When a drug is present in the sample, the drug and the conjugate traverse the strip together. The more drug in the sample, the further the conjugate and drug move toward the predetermined site. If neither drug is present in the sample, then all of each of the conjugates will be bound by antibodies for the drugs and captured prior to reaching the predetermined site. If one or both drugs are present above the predetermined minimum amounts, one or both of the conjugates will move to the predetermined site. In subsequent development of the test strip by contact with enzyme substrates, the presence of one or more of a given drug in the sample will be indicated by production of a signal at the predetermined site.

In this procedure the test solution can traverse all or part of the strip by capillary action. If the test solution is allowed to traverse the entire strip past the predetermined site, the strip can subsequently be immersed in the developer solution containing the enzyme substrates. In a variant of the above-described embodiment, the volume of the test solution may be sufficient to permit it to traverse only a portion of the strip such that the fluid capacity at the dry portion of the strip is at least as great as the fluid capacity of the portion from the contact portion to the predetermined site. The contact portion of the strip can then be contacted with the developer solution. The developer solution moves along the strip by capillarity. In doing so, the developer solution causes the remainder of the test solution to move past the predetermined site. If one or more of the analytes is present in the test solution, a signal is generated.

As a matter of convenience, the present device can be provided in a kit in packaged combination with predetermined amounts of reagents for use in assaying for an analyte or a plurality of analytes. Where an enzyme is used as the label, the reagents will include enzyme labeled analyte and the developer solution can contain substrate for the enzyme or precursors therefor including any additional substrates, enzymes and cofactors and any reaction partner of the enzymic product required to provide the detectable chromophore or fluorophore. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The invention is further demonstrated by the following illustrative examples. Temperatures are in degrees Centigrade (°C.).

EXAMPLE 1

Preparation of Conjugates of HRP

Into a reaction flask was introduced 8.1 mg of 1-methyl-3-(3'-carboxypropyl)xanthine, 3.8 mg of N-hydroxysuccinimide (NHS), 6.7 mg 1-ethyl-3-(dimethylaminopropyl)carbodiimide (EDCI) and 125 µl dimethylformamide (DMF) and the mixture allowed to stand overnight at room temperature.

To a 1.3 ml sample of HRP-oxyamine (1 mg) in 0.1M sodium carbonate, pH 9.0, was added the ester prepared above. To this end 0.217 ml of DMF and 66 µl of the above ester preparation were combined and added in 8.25 µl increments over a period of about 2 h. During the addition, the temperature was maintained at 4°, and the mixture then allowed to stand overnight at 4°.

The reaction mixtures were then chromatographed on G-25 Sephadex ® with standard buffer.

Conjugates of HRP with phenobarbital, phenytoin, carbamazepine, and morphine were also prepared in a similar manner.

Reagents 0.1M phosphate buffer with 0.2M NaCl pH 7.0.
2.0 mg/ml bovine gamma globulin.
0.1 mg/ml glucose oxidase.
0.05% Triton QS-15 detergent (Sigma Chemical Co., St. Louis, Mo.).
HRP-conjugate, one, or all of the following: 0.25 µg/ml HRP-theophylline, 0.50 µg/ml HRP-phenobarbital, 0.15 µg/ml HRP-phenytoin, 2.00 µg/ml HRP-carbamazepine.

Developer Solution 1.17 gm/L $NaH_2PO_4$.
0.90 gm/L $Na_2HPO_4$.
50 mM beta D-(+)-glucose.
400 µg/ml 4-chloro-1-naphthol.
20 µL/ml N,N-dimethylformamide.
0.05% Triton QS-44 pH 6.5.

Paper Preparation

Solutions:
(1) dipping solution-pH 9.5
  0.1M sodium bicarbonate buffer
  2 mg/ml specific antibody for phenytoin (or a mixture of antibodies for phenytoin, phenobarbital, theophylline, and carbamazepine)+sheep immunoglobulin
(2) capping solution pH 9.5
  0.3M ethanolamine
  0.15M HCL
(3) wash solution
  0.1M phosphate+0.2M NaCl pH 7.0
  deionized water
(4) preservative
  0.6% polyvinyl alcohol 20/30
(5) Procedure:
Carbonyldimimidizole activated Whatman 31 ET paper was immersed in the dipping solution and incubated for one hour at room temperature. The paper was treated with the capping solution overnight at room temperature. The paper was washed twice with the phosphate buffer, and once with deionized water for 20 minutes each. The paper was preserved by soaking it in the preservative for about 20 minutes. The paper was dried for about 8 minutes at 65° C. in a tunnel dryer.

Assay Protocol 1.0 ml of the test solution was dispensed into a 16×100 mm test tube and 12.0 µl of a calibrator containing one, or all, of the test analytes (theophylline, phenobarbital, phenytoin, and carbamazepine) was added. One strip of prepared paper was placed in the tube together with the test solution, which was allowed to wick up the paper by capillary action for 15 minutes at room temperature. The strip was then transferred to a second 16×100 mm tube containing 10 mls of developer solution. The strip was removed from the developer after 5 minutes. The strip was examined for the presence of a blue color.

A. Single system—one analyte in the test solution

The test solution contained HRP-phenytoin and 12 μl of each phenytoin calibrator. The paper contained only phenytoin specific antibody.

B. Multiple system—all of the above analytes in the test solution

The test solution contained all for HRP-analyte conjugates, and 12 μl of calibrators containing all four analytes. The paper contained all four specific antibodies mentioned above.

Results

Table 1

| Calibrator conc. (μg/ml) | single system (A) (mm) | multiple system (B) (mm) |
| --- | --- | --- |
| 0 | 16 | 16 |
| 1.5 | 23 | 23 |
| 7.5 | 44 | 45 |
| 10.0 | 48 | 48 |
| 20.0 | 60 | 62 |
| 25.0 | 66 | 67 |

The single and multiple systems yielded equivalent results, which indicates that the device and method of the present invention can be utilized to determine the presence of one or more analytes in a sample. Depending on the particular predetermined minimum amount of drug suspected of being in the test solution, a predetermined site can be set on the bibulous material with reference to the data in Table 1.

EXAMPLE 2

The assays summarized below in Table 2 were conducted using reagents prepared and methods employed similar to those described in Example 1. The results are the average of three separate runs and are set forth in Tables 2-5 below.

TABLE 2

| One antibody, one enzyme conjugate, one drug system | | |
| --- | --- | --- |
| | Migration height (mm) | |
| Drug | 0 μg/ml | 0.3 μg/ml |
| morphine | 24 | 59 |
| methadone | 27 | 54 |
| phenobarbital | 24 | 57 |
| benzoylecgonine | 15 | 59 |
| theophylline | 21 | 59 |

TABLE 3

| Five antibodies, one enzyme conjugate, one drug system | | |
| --- | --- | --- |
| | Migration height (mm) | |
| Drug | 0 μg/ml | 0.3 μg/ml |
| morphine | 27 | 65 |
| methadone | 26 | 55 |
| phenobarbital | 26 | 61 |
| benzoylecgonine | 17 | 69 |
| theophylline | 19 | 60 |

TABLE 4

| Five antibodies, five enzyme conjugates, one drug system | | |
| --- | --- | --- |
| | Migration height (mm) | |
| Drug | 0 μg/ml | 0.3 μg/ml |
| morphine | 29 | 63 |
| methadone | 31 | 56 |

TABLE 4-continued

| Five antibodies, five enzyme conjugates, one drug system | | |
| --- | --- | --- |
| | Migration height (mm) | |
| Drug | 0 μg/ml | 0.3 μg/ml |
| phenobarbital | 31 | 60 |
| benzoylecgonine | 30 | 67 |
| theophylline | 29 | 59 |

TABLE 5

| Five antibodies, five enzyme conjugates, five drug system | | |
| --- | --- | --- |
| | Migration height (mm) | |
| Drug | 0 μg/ml | 0.3 μg/ml |
| morphine, methadone, phenobarbital, benzoylecgonine, theophylline | 28 | 60–69 |

The above data indicate that the device and method of the present invention can be utilized to determine the presence of one or more analytes in a sample suspected of containing one or more analytes. Depending on the particular predetermined minimum amount of drug suspected of being in the test solution, a predetermined site can be set on the bibulous material with reference to the data in Tables 2-5.

The invention has been described in detail with particular reference to the above embodiments. It will be understood, however, that variations and modifications can be effected within the spirit and scope of the invention.

What is claimed is:

1. A method for determining the presence at or above a predetermined minimum detectible amount of one or more of a plurality of analytes in a sample suspected of containing one or more of said analytes, each analyte being a member of a specific binding pair ("sbp member") consisting of ligand and its complementary receptor, which method comprises (a) contacting, with a test solution containing said sample and predetermined amounts of two or more first sbp members each respectively analogous to one of said analytes, a contact portion of a piece of bibulous material capable of being traversed in at least one direction by said test solution by capillary migration, said bibulous material having substantially uniformly and non-diffusively bound thereto predetermined amounts of two or more second sbp members each respectively capable of binding one of said analytes and said first sbp members such that in the presence of a predetermined amount of each analyte the analogous first sbp member migrates at least to a predetermined site on said piece of bibulous material separated from said contact portion, (b) allowing at least a portion of the test solution to traverse said bibulous material by means of capillary migration at least to said predetermined site, and (c) detecting one or more of said first sbp members at said predetermined site.

2. The method of claim 1 wherein said first sbp member is detected by exposing said bibulous material to a signal producing means capable of interacting with said first sbp members to produce a detectible signal, the presence of said signal at said predetermined site indicating the presence of one or more of said analytes in said sample.

3. The method of claim 1 wherein the presence of said first sbp member at said predetermined site is detected directly by examining said predetermined site for the presence of a signal.

4. The method of claim 1 wherein said piece of bibulous material is a strip.

5. The method of claim 4 wherein said strip is a paper strip.

6. The method of claim 1 wherein each of said second sbp members is a respective antibody for an analyte.

7. The method of claim 1 wherein each of said first sbp members is respectively conjugated to a label.

8. The method of claim 7 wherein said label is an enzyme.

9. The method of claim 8 wherein a second enzyme is bound uniformly to said bibulous material at least over an area including said predetermined site, the enzymes being related in that the product of one enzyme is the substrate for the other.

10. The method of claim 1 wherein each of the analytes is a drug, each of said first sbp members is a corresponding drug analog conjugated to a label, and each of said second sbp members is respectively a corresponding antibody to one of said drugs.

11. The method of claim 1 wherein said test solution is allowed to traverse said bibulous material past said predetermined site in step (b).

12. The method of claim 2 wherein said signal producing means comprises a substrate and each of said first sbp members is conjugated to a catalyst.

13. The method of claim 12 wherein at least a portion of said bibulous material including said predetermined site is immersed in a solution of said substrate.

14. The method of claim 12 wherein an end portion of said bibulous material is contacted with a solution of said substrate which is allowed to traverse said bibulous material past said predetermined site by means of capillary migration.

15. The method of claim 1 wherein said bibulous material contains means associated therewith for allowing detection of one or more of a said first sbp members only at said predetermined site.

16. The method of claim 15 wherein said means conceals from view the portion of the bibulous material between said contact portion and said predetermined site.

17. The method of claim 15 wherein said means is an enclosure with an opening for viewing said predetermined site.

18. The method of claim 15 wherein said means is a signal inhibitor that inhibits signal formation except at said predetermined site.

19. The method of claim 15 wherein said means is an enzyme bound to said bibulous material only at said predetermined site and said first sbp member is conjugated to an enzyme wherein the enzymes are related in that the product of one is the substrate for the other.

20. A method for determining the presence at or above a predetermined minimum detectible amount of one or more of a plurality of analytes in a sample suspected of containing one or more of said analytes, which method comprises
(a) contacting, with a test solution containing said sample and a predetermined amount of two or more analyte analogs each conjugated to an enzyme, the end portion of a strip of bibulous material capable of being traversed by said test solution by capillary migration, said strip having substantially uniformly and non-diffusively bound thereto predetermined amounts of two or more antibodies, each respectively capable of binding one of said analyte analogs and its corresponding analyte, such that in the presence of a predetermined amount of each analyte the corresponding analyte analog migrates at least to a predetermined site on said strip separated from said end portion,
(b) allowing at least a portion of the test solution to traverse said strip past said predetermined site by capillary migration, and
(c) examining said predetermined site for the presence of one or more of said analyte analogs, the presence thereof indicating the presence of one or more analytes in said sample.

21. The method of claim 20 wherein said predetermined site is examined by contacting said strip at least at said predetermined site with a developer solution containing members of a signal producing system other than said enzymes, said signal producing system being capable of producing a detectible signal at said predetermined site in relation to the presence of one or more of said analytes in the test solution.

22. The method of claim 20 wherein said predetermined site is examined directly for the presence of a signal.

23. The method of claim 20 wherein said strip of bibulous material is a paper strip.

24. The method of claim 20 wherein each of said analytes is a drug.

25. The method of claim 20 wherein one of said analytes is a drug.

26. The method of claim 20 wherein a second enzyme is bound to said strip, the enzymes being related in that the product of one enzyme is the substrate of the other.

27. The method of claim 20 wherein each of said analytes is a non-drug.

28. The method of claim 21 wherein said strip is immersed in said developer solution.

29. The method of claim 21 wherein the end portion of said strip is contacted with said developer solution which is allowed to traverse said strip past said predetermined site by means of capillary migration.

30. The method of claim 20 wherein said strip contains means associated therewith for allowing the presence of one or more of said analyte analogs to be viewed only at said predetermined site.

31. The method of claim 30 wherein said means conceals from view the portion of the strip between said end portion and said predetermined site.

32. The method of claim 30 wherein said means is a signal inhibitor that inhibits signal formation except at said predetermined site.

33. The method of claim 30 wherein said means is a second enzyme bound to said strip only at said predetermined site and the enzyme bound to said analyte analog and said second enzyme are related in that the product of one is the substrate for the other.

34. The method of claim 30 wherein said means is an enclosure with an opening for viewing said predetermined site.

35. A device for determining the presence at or above a predetermined minimum amount of one or more of a plurality of analytes in a test solution containing predetermined amounts of two or more first sbp members, each respectively analogous to one of said analytes, each analyte being a member of a specific binding pair, said device comprising a piece of bibulous material capable of traversal by said test solution in at least one direction by capillary migration, said bibulous material having a contact portion for contacting said test solution and a predetermined site separated from said contact portion and predetermined amounts of two or more second sbp members each respectively complementary to one of said analytes substantially uniformly and non-diffusively bound to said bibulous material at least between said contact portion and said predetermined site, said predetermined amounts of said second sbp members being such that in the presence at or above a predetermined minimum detectible amount of at least one of said analytes a first sbp member migrates to said predetermined site on said bibulous material and means associated with said bibulous material for allowing detection of one or more of said first sbp members only at said predetermined site, wherein each of said sbp members is respectively conjugated to an enzyme and said means is a second enzyme bound to said bibulous material only at said predetermined site, the enzymes being related in that the product of one enzyme is the substrate for the other.

36. A device for determining the presence at or above a predetermined minimum amount of one or more of a plurality of analytes in a test solution containing predetermined amounts of two or more first sbp members, each respectively analogous to one of said analytes, each analyte being a member of a specific binding pair, said device comprising a piece of bibulous material capable of traversal by said test solution in at least one direction by capillary migration, said bibulous material having a contact portion for contacting said test solution and a predetermined site separated from said contact portion and predetermined amounts of two or more second sbp members each respectively complementary to one of said analytes substantially uniformly and non-diffusively bound to said bibulous material at least between said contact portion and said predetermined site, said predetermined amounts of said second sbp members being such that in the presence at or above a predetermined minimum detectible amount of at least one of said analytes a first sbp member migrates to said predetermined site on said bibulous material and means associated with said bibulous material for allowing detection of one or more of said first sbp members only at said predetermined site, wherein said means is a signal inhibitor bound to said strip between said contact portion and said predetermined site.

* * * * *